United States Patent [19]

Inagaki et al.

[11] Patent Number: 4,797,476
[45] Date of Patent: Jan. 10, 1989

[54] MONO-4-ARYLAZOARYL PHOSPHORIC ESTERS

[75] Inventors: Yoshio Inagaki; Masaki Okazaki, both of Minami-ashigara, Japan

[73] Assignee: Fuji Shashin Film Kabushiki Kaisha, Japan

[21] Appl. No.: 906,098

[22] Filed: Sep. 10, 1986

Related U.S. Application Data

[63] Continuation of Ser. No. 749,014, Jun. 26, 1985, abandoned, which is a continuation of Ser. No. 360,211, Mar. 22, 1982, abandoned.

[30] Foreign Application Priority Data

Mar. 26, 1981 [JP] Japan ................................. 56-44325

[51] Int. Cl.$^4$ ............... C07C 107/06; C07C 107/08; C09B 43/00; C09B 62/825
[52] U.S. Cl. ........................ 534/727; 435/39; 436/106; 436/164; 514/150; 534/588; 534/593; 534/617; 534/887
[58] Field of Search ............................... 534/727, 617

[56] References Cited

U.S. PATENT DOCUMENTS

| | | | |
|---|---|---|---|
| 2,947,663 | 8/1960 | Losco et al. | 534/727 X |
| 2,959,582 | 11/1960 | Schimmelschmidt et al. | 534/727 X |
| 3,947,435 | 3/1976 | Pechmeze et al. | 534/727 X |
| 4,051,240 | 9/1977 | Oswald et al. | 534/727 X |
| 4,052,381 | 10/1977 | Schrider et al. | 534/727 X |

OTHER PUBLICATIONS

Chemical Abstracts, 9th Collective Index, vols. 76–85, Formulas $C_{12}H_{10}N_2O_3$ – $C_{14}H_{18}F_6O_6$, p. 5374R $C_{15}H_{11}N_2O_4P$ (1978).

Chlebowski et al, J. Biolog. Chem., vol. 249, No. 22, pp. 7192 to 7202 (1974).

Mushak et al, Biochem., vol. 11, No. 2, pp. 201 to 205 (1972).

Loveless et al, Quarterly Journal of Microscopial Science, vol. 90(1), pp. 57–67 (1949).

*Primary Examiner*—Floyd D. Higel
*Attorney, Agent, or Firm*—Jacobs & Jacobs

[57] ABSTRACT

New phosphoric ester having the following formula (I) and a method for the analysis of an alkaline phosphatase, using the phosphoric ester as a substrate:

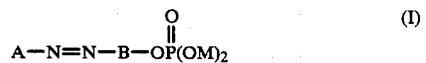

(I)

wherein M is a hydrogen atom or an alkali metal atom; A is phenyl, naphthyl, 2- or 4-pyridyl, 2- or 4-pyrimidyl, pyrazinyl, sym-triazinyl, 2-imidazolyl, 2-oxazolyl, 2-thiazolyl, or sym-thiadiazolyl group which may or may not be substituted with other substituent(s) or may form a condensed ring together with a benzene ring, if possible; B is paraphenylene group or may form naphthylene group by condensation together with a benzene ring, said groups may or may not be substituted with other substituent(s).

13 Claims, 5 Drawing Sheets

MONO-4-ARYLAZOARYL PHOSPHORIC ESTERS

This is a continuation of Ser. No. 749,014 filed 06/26/85, now abandoned which is a continuation of Ser. No. 360,211 filed 03/22/82, now abandoned.

BACKGROUND OF THE INVENTION

1. Field of the Invention

This invention relates to novel monoesters of phosphoric acid and more particularly, novel phosphoric esters which are hydrolyzed by the action of an alkaline phosphatase to release an azo dye and a method for the analysis of the alkaline phosphatase, using the ester as a substrate.

It is very important for a clinical examination to see the activity of an alkaline phosphatase in human body fluid. It is well known that when the activity of an alkaline phosphatase is high, metabolism in the liver, bones, or the like is generally under the unfavourable conditions and therefore, symptons of liver disease, rickets, osteosarcoma, dysthyroidism, or the like appear. Accordingly, it is quite, natural that various methods for the determination of an alkaline phosphatase activity have been proposed.

It is required that a method for the quantitative determination of an alkaline phosphatase used in an ordinary clinical examination is simple in operation and has a good reproducibility. For this purpose, there are so-called a colorimetry and a fluorometry.

The colorimetry is a method of quantitative analysis in which a compound which is hydrolyzed by the action of an alkaline phosphatase to release a dye or a dye-precursor is used as a substrate of an enzymatic reaction, and the dye released in the enzymatic reaction is colorimetrically measured or the dye-precursor released in the enzymatic reaction is reacted with a reagent thereby to be converted into the dye which is then colorimetrically measured to determine the activitiy of the alkaline phosphatase. The colorimetry has an advance that a colorimeter or a spectrophotometer which are widely spread may be conveniently utilized to conduct the analysis. On the other hand, the fluorometry is a method of quantitative analysis in which a compound which is hydrolyzed by the action of an alkaline phosphatase to release a fluorescent substance is used as a substrate of an enzymatic reaction, and a fluorescent intensity of the fluorescent substance released in the enzymatic reaction is measured to thereby determine the activity of the alkaline phosphatase. The fluorometry has a higher sensitivity as compared with the colorimetry, however it has some disadvantages that it is apt to be disturbed by a trace of fluorescent substance which may coexist therewith and a fluorometer has not so widely spread.

This invention relates to novel mono-4-arylazoaryl phosphoric esters which may be used as a suitable substrate in a method for the quantitative analysis of an alkaline phosphatase by a colorimetry.

2. Description of the Prior Art

In the past, there have been used the following methods for the quantitative analysis of an alkaline phosphatase by a colorimetry.

(1) The method in which disodium p-nitrophenyl phosphate is used as a substrate and p-nitrophenol which is released on hydrolysis of the substrate by the action of an alkaline phosphatase is colorimetrically measured to determine the activity of the alkaline phosphatase, which is specifically described in O. A. Bessey, O. H. Lowry and M. J. Brock, "Journal of Biological Chemistry", Vol. 164, p. 321 (1946).

(2) The method in which phenolphthalein phosphate is used as a substrate and phenolphthalein which is released on hydrolysis of the substrate by the action of an alkaline phosphatase is colorimetrically measured to determine the activity of the alkaline phosphatase, which is specifically described in A. L. Babson, S. J. Greeley, C. M. Coleman, and G. E. Phillips, "Clinical Chemistry", Vol. 12, p. 482 (1966).

(3) The method in which thymolphthalein phosphate is used as a substrate and thymolphthalein which is released on hydrolysis of the substrate by the action of an alkaline phosphatase is colorimetrically measured to determine the activity of the alkaline phosphatase, which is specifically described in C. M. Colemann, "Clinical Chemistry", Vol. 13, p. 401 (1966).

(4) The method in which thymolblue mono-phosphate is used as a substrate and thymolblue released on hydrolysis of the substrate by the action of an alkaline phosphatase is colorimetrically measured to determine the activity of the alkaline phosphatase, which is specifically described in Japanese Patent Disclosure (OPI) No. 136662/1976.

(5) The method in which phenyl phosphate is used as a substrate and phenol released on hydrolysis of the substrate by the action of an alkaline phosphatase is oxidatively condensed with 4-amino-antipyrine in the presence of potassium ferricyanide to form red quinone which is colorimetrically measured to determine the activity of the alkaline phosphatase, which is specifically described in P. R. N. Kind and E. J. King, "Clinical Pathology", Vol. 7, p. 322 (1954); K. Watanabe et al., "Rinsho-Byori or Clinical Pathology", Vol. 15, p. 708 (1967); T. Nakayama et al., "Rinsho-Byori or Clinical Pathology", Vol 23 (a supplementary volume in the general meeting), p. 85 (1975).

Among the methods in the prior art described above, the method (1) is most widely used as a method for the quantitative analysis of an alkaline phosphatase, however, the colorimetry is carried out at 410 nm and therefore, this method is interfered with a colored substance such as bilirubin, hemoglobin, etc. contained in serum and thus, it requires a blank test which makes operations more complicate. The prior methods (2) to (5) tentatively overcome the disadvantage of the method (1) because a colorimetry in the methods (2) to (5) is conducted at a longer wavelength region than that in method (1). However, it is difficult to synthesyze highly pure mono-phosphoric esters of phthaleins which are used as a substrate in the methods (2) to (4). In other words, these mono-phosphoric esters may be obtained by hydrolysis of monophosphorodichloridate of corresponding phthalein which may be prepared by reacting one hydroxyl group of the phthalein molecule with phosphorous oxychloride. In this reaction, a higher molar ratio of phosphorous oxychloride to phthalein causes phosphorylation of more than one hydroxyl group, while a lower molar ratio thereof causes formation of two or three kinds of products since one molecule of phosphorous oxychloride reacts with two or three molecules of phthalein. In either case, an unsuitable compound for a substrate to be used in the quantitative analysis of an alkaline phosphatase is produced as a secondary product. Accordingly, the isolation and purification of the product after the reaction require a troublesome operation and as the result, it is difficult to obtain products having a high degree of purity. On the other hand, the method (5) of the prior art comprises the two step reactions of an enzymatic, phenol-release reaction and subsequent coloring reaction, which require complicated operations.

Thus, it has been expected that an improved method for the quantitative analysis of an alkaline phosphatase without the disadvantages described above would appear.

SUMMARY OF THE INVENTION

Accordingly, it is an object of the present invention to provide a new substrate to be used for the quantitative analysis of an alkaline phosphatase, the substrate being excellent in operations at the time of measurement, having no susceptibility to interference with a colored substance such as a pigment in blood, having a high sensitivity, and being easily synthesized and purified.

It has been found that the above mentioned object can effectively be accomplished by a novel phosphoric ester having the following general formula (I):

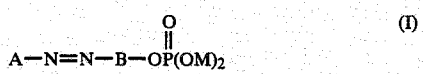

wherein M is a hydrogen atom or an alkali metal atom such as a sodium or a potassium atom; A is phenyl, naphthyl, 2- or 4-pyridyl, 2- or 4-pyrimidyl, pyrazinyl, sym-triazyl, 2-imidazolyl, 2-oxazolyl, 2-thiazolyl, or sym-thiadiazolyl group which may or may not be substituted with other substituent(s) or may form a condensed ring together with a benzene ring, if possible; B is para-phenylene group or may form naphthylene group by condensation together with a benzene ring, which may or may not be substituted with other substituent(s).

DETAILED DESCRIPTON OF THE PREFERRED EMBODIMENTS

Figure 1:
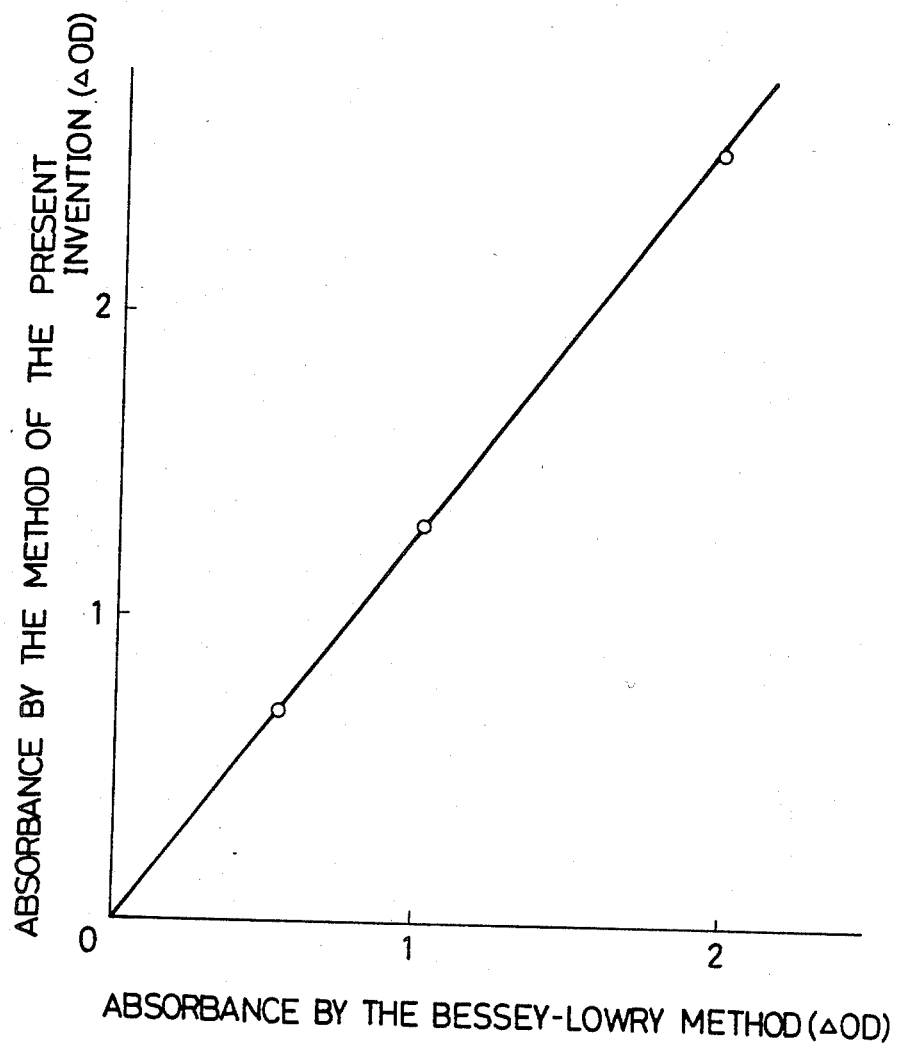
FIGS. 1 to 5 are graphs showing a relationship between two absorbances (ΔOD) measured by the Bessey-Lowry method, which is shown on the abscissa, and by the method in which a compound of the present invention is used as a substrate, which is shown on the ordinate respectively.

The radical A in the general formula (I) may be substituted with a substituent or substituents such as a halogen atom, a nitro, an alkanesulfonyl (preferably from 1 to 4 carbon atoms), a trifluoromethyl, a sulfonamido (preferably from 1 to 7 carbon atoms), a sulfamoyl (preferably less than 8 carbon atoms), an alkyl (preferably less than 8 carbon atoms), an alkoxy (preferably less than 5 carbon atoms and may be substituted with an alkoxy or other groups), an alkylthio (preferably less than 5 carbon atoms), a phenoxy (may be substituted with halogen atom(s)), an anisyl, a toluyl, an arylthio (preferably less than 8 carbon atoms) group, or the like.

A paraphenylene or a naphthylene groups represented by B in the general formula (I) may be substituted with a substituent or substituents such as a lower alkyl (preferably from 1 to 4 carbon atoms), a lower alkoxy (preferably from 1 to 4 carbon atoms), a lower alkylthio (preferably from 1 to 4 carbon atoms), a sulfonamid (preferably from 1 to 7 carbon atoms), a sulfamoyl (preferably less than 8 carbon atoms), a carboxamido (preferably from 1 to 7 carbon atoms), a carbamoyl (preferably less than 8 carbon atoms), hydroxyl, or the like.

All the compounds represented by the general formula (I) are hydrolyzed by the action of an alkaline phosphatase at a rate being in proportion to the activity of the alkaline phosphatase to release the corresponding azo dye so that the compounds may be used as a substrate for the quantitative analysis of the alkaline phosphatase. In view of the easiness of synthesis, suitability of wavelength at which a colorimetry is conducted, solubility, and sensitivity, the preferred compounds are those represented by the general formula (I) wherein M is a hydrogen, a sodium, or a potassium atom; A is a halogen atom, a nitro, an alkanesulfonyl having from 1 to 4 carbon atoms, a trifluoromethyl, a sulfonamido having from 1 to 7 carbon atoms, a sulfamoyl having less than 8 carbon atoms, an alkyl having less than 5 carbon atoms, an alkoxy having less than 5 carbon atoms, an alkylthio having less than 5 carbon atoms, an alkoxy-substituted alkoxy having less than 5 carbon atoms, a phenoxy, a halogen-substituted phenoxy, an anisyl, a toluyl, a phenyl substituted with one or more arylthio groups having less than 8 carbon atoms, or a phenyl group; B is a paraphenylene group, or may form a naphthylene group by condensation together with a benzene ring, the paraphenylene or the naphthylene group may be substituted with one or more groups selected from a halogen atom, a lower alkyl having from 1 to 4 carbon atoms, a lower alkoxy having from 1 to 4 carbon atoms, an alkylthio having from 1 to 4 carbon atoms, a sulfonamido having from 1 to 7 carbon atoms, a sulfamoyl having less than 8 carbon atoms, a carboxamido having from 1 to 7 carbon atoms, a carbamoyl having less than 8 carbon atoms, or a hydroxyl group.

Among the compounds represented by the general formula (I), the compounds represented by the following general formula (II) are more preferable due to their good stability.

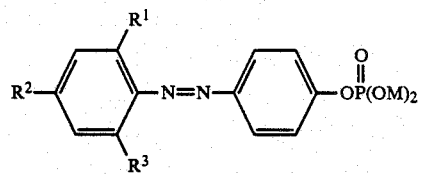

wherein M is a sodium or a potassium atom; $R^1$ is a hydrogen, a fluorine or a chlorine atom, a nitro, a methanesulfonyl, or a trifluoromethyl group; $R^2$ is a hydrogen, a fluorine or a chlorine atom, a nitro, a methanesulfonyl, or a trifluoromethyl group; $R^3$ is a hydrogen, a fluorine or a chlorine atom.

The compounds of the formula (II) wherein at least one of $R^1$ and $R^2$ is a nitro or a methanesulfonyl group; $R^3$ is a hydrogen or a chlorine atom are preferable since their starting materials are easily available.

The compounds of the formula (II) wherein at least one of $R^1$ and $R^2$ is a nitro or a methanesulfonyl group are preferable since a dye released on hydrolysis of the compound by the action of an alkaline phosphatase have a large absorption maximum wavelength on the visible light absorption spectrum and have a large molecular extinction coefficient.

The compounds represented by the general formula (I) will now be described with reference to the following specific examples to which the scope of the present invention is not limited.

Compound 1:

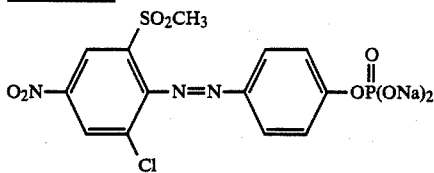

Compound 2:
The same as Compound 1 except for a case where K is substituted for Na.

Compound 3:

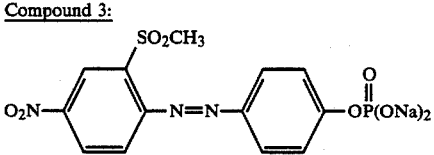

Compound 4:
The same as Compound 3 except for a case where K is substituted for Na.

Compound 5:

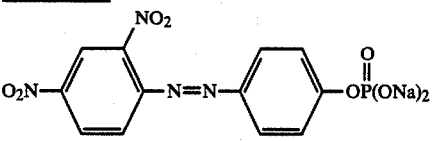

Compound 6:
The same as Compound 5 except for a case where K is substituted for Na.

Compound 7:

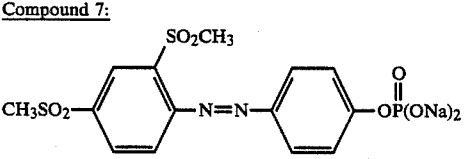

Compound 8:
The same as Compound 7 except for a case where K is substituted for Na.

Compound 9:

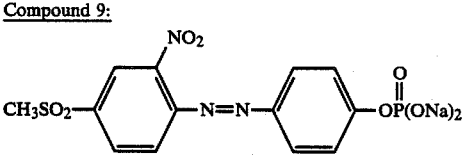

Compound 10:
The same as Compound 9 except for a case where K is substituted for Na.

Compound 11:

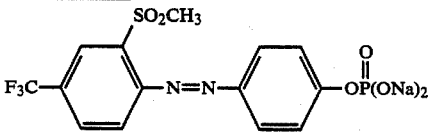

Compound 12:
The same as Compound 11 except for a case where K is substituted for Na.

Compound 13:

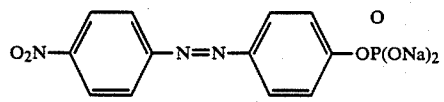

Compound 14:
The same as Compound 13 except for a case where K is substituted for Na.

Compound 15:
The same as Compound 13 except for a case where H is substituted for Na.

Compound 16:

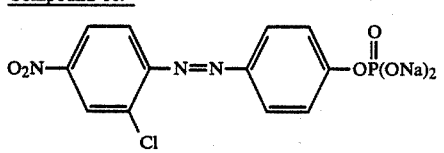

Compound 17:
The same as Compound 16 except for a case where K is substituted for Na.

Compound 18:
The same as Compound 16 except for a case where H is substituted for Na.

Compound 19:

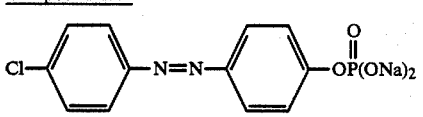

Compound 20:
The same as Compound 19 except for a case where K is substituted for Na.

Compound 21:
The same as Compound 19 except for a case where H is substituted for Na.

Compound 22:

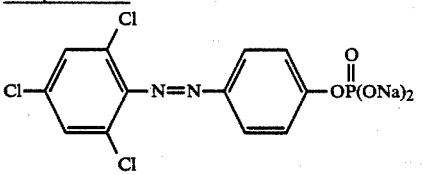

Compound 23:
The same as Compound 22 except for a case where K is substituted for Na.

Compound 24:
The same as Compound 22 except for a case where H is substituted for Na.

Compound 25:

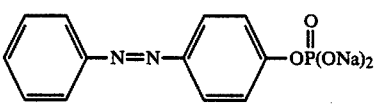

Compound 26:
The same as Compound 25 except for a case where K is substituted for Na.

Compound 27:
The same as Compound 25 except for a case where H is substituted for Na.

-continued
Compound 28:
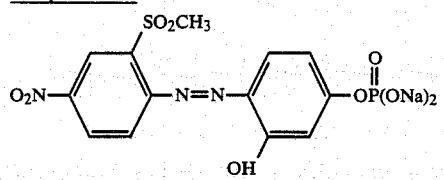
Compound 29:
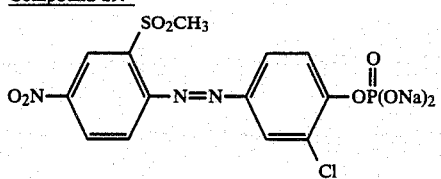
Compound 30:
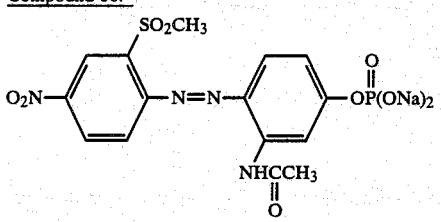
Compound 31:
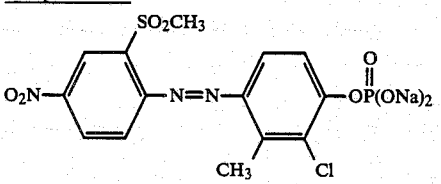
Compound 32:
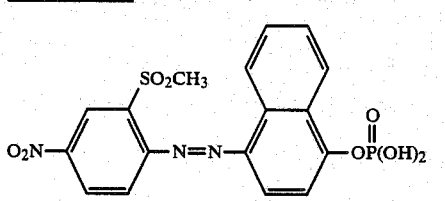
Compound 33:
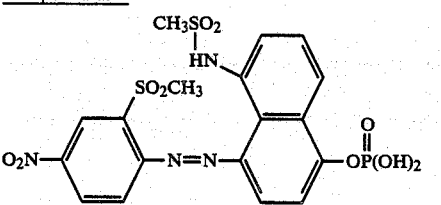
Compound 34:
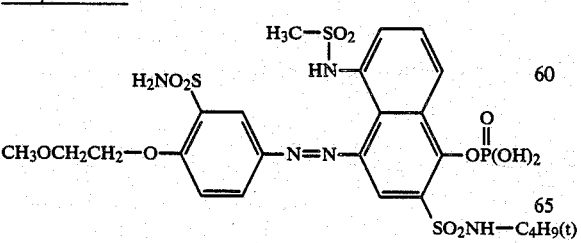
Compound 35:
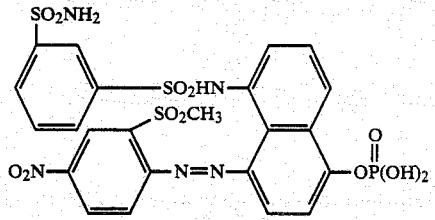
Compound 36:
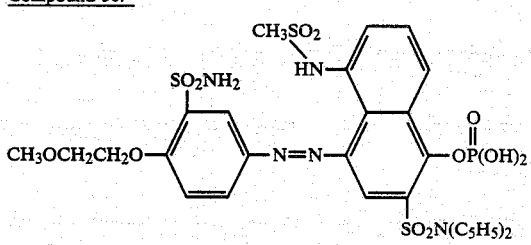
Compound 37:
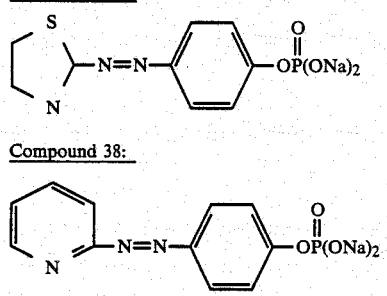
Compound 38:
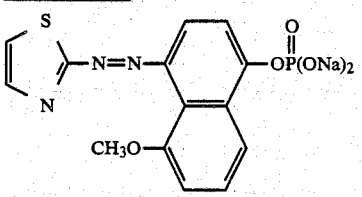
Compound 39:
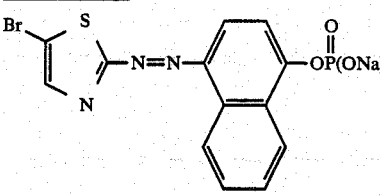
Compound 40:
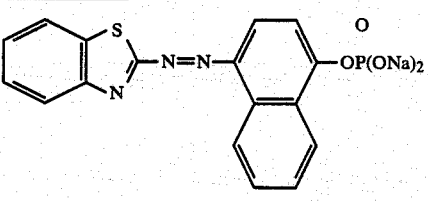
Compound 41:
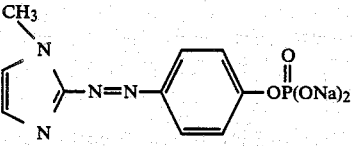
Compound 42:

-continued

Compound 43:

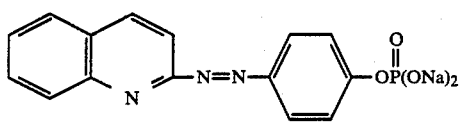

Compound 44:

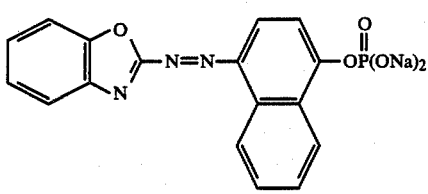

Compound 45:

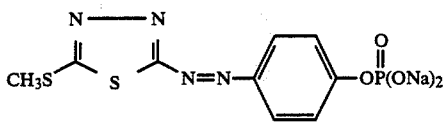

Compound 46:

Compound 47:

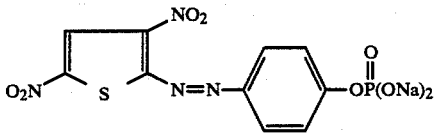

Now, a method for the synthesis of the compounds of the formula (I) will be explained. First, a diazo coupling reaction between an aromatic amine (III) and a phenol derivative H—B—OH is conducted by a conventional manner to produce an azo dye (IV). In cases where the radical A has a strong electron withdrawing group of which the Hammett's sigma constant is above 0.5 such as a nitro or a methanesulfonyl or where the sum of the Hammett's sigma constants of substituents on the radical A is above 0.5, preferably, the so-called nitrosyl sulfuric acid process of which specific example is described in, for example, S. R. Sandler and W. Karo, "Organic Functional Group Preparations", Vol. 2, p. 295, Academic Press, (1971), may be used for the synthesis of diazonium salt formed by diazotization of the compound (III).

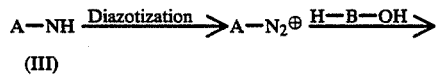

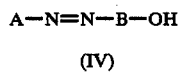

The azo dye (IV) is then reacted with a large excess of phosphorous oxychloride in the presence of pyridine to produce phosphorodichloridate (V) which is then reacted with water to obtain phosphoric monoester (I').

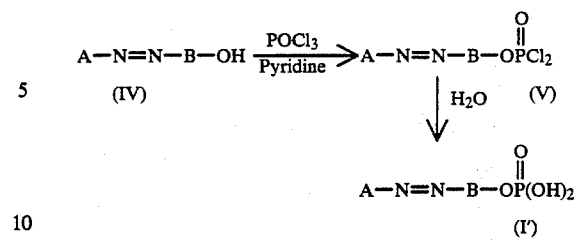

In the reaction in which the compound (V) is obtained from the compound (IV), it has been found that the compound (IV) can be converted to the compound (V) with almost no byproducts by dropping a solution of the compound (IV) in pyridine, pyridine-containing acetone, pyridine-containing trimethyl phosphate, or a mixed solvent of pyridine-containing acetone and trimethyl phosphate to a ½ to 1/50, preferably 1/5 to 1/10 solution of more than 3 moles, preferably from 3 to 10 moles of phosphorous oxychloride based on one mole of the compound (IV) in acetone, trimethyl phosphate, or a mixed solvent thereof, at from −15° C. to 10° C., preferably from −10° C. to 0° C. Instead of pyridine, a tertiary amine having a higher basicity than that of pyridine, such as triethylamine, may be added to the solution of the compound (IV). The formation of the compound (V) can be confirmed by a silica gel thin layer chromatography in which a spot having Rf value smaller than that of the compound (IV) appears. In the past, an aryl phosphorodichloridate such as p-nitrophenyl phosphorodichloridate was synthesized by reacting phosphorus oxychloride with phenols under refluxing in the presence of potassium chloride, or the like, of which specific example is described in, for example, Mukaiyama and Hashimoto, "Bulletin of the Chemical Society of Japan", Vol. 44, 196 (1971).

However, the compound (V) of the present invention was inefficiently produced under such severe conditions.

The conversion of the compound (V) into the compound (I') may be carried out by the addition of water to the reaction liquid without the isolation of the compound (V). Under an acidic condition, the compound (I') may be occasionally decomposed and therefore, in the reaction between the compound (V) and water, a tertiary amine such as pyridine may be added to capture the hydrogen chloride produced therein, or a water-immiscible solvent such as ethylacetate may be added to form a two-layer reaction system of water and oil, such modifications of the reaction may bring about good results.

The cmpound (I') thus obtained is dissolved in an aqueous solution of sodium or potassium hydroxides. After adjusting the pH of the resulting solution to around 10, insolubles are removed by filtration, the resulting solution is dropped to ethanol having a volume by about 10 to 20 times as much as that of the solution with agitation, and then crystals of the compound (I) are obtained.

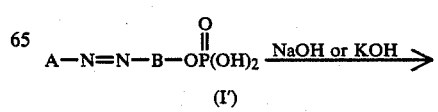

-continued

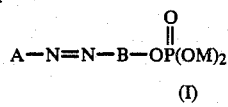

(I)

The compound (I) thus obtained is dissolved in a small amount of water. The resulting solution is poured into ethanol, and the purified compound (I) is crystallized out.

The crystalline compound (I) obtained by the process described above often contains one or a few molecules of water of crystallization.

The compound of the present invention thus synthesized and represented by the general formula (I) is an excellent substrate to be used for the quantitative analysis of an alkaline phosphatase. In other words, the compound represented by the formula (I) has the following advantages: (1) the compound is hydrolyzed by the action of an alkaline phosphatase at a rate being in proportion to the activity of the alkaline phosphatase to release an azophenol dye, (2) the dye shows the maximum absorption of visible light in the longer wavelength region as compared with p-nitrophenol which is a dye released in the conventional method in which disodium p-nitrophenol phosphate is used as a substrate, and so much the interference with colored substances, such as pigments in blood, decreases, and (3) the compund (I) may be synthesized with no difficulty, as shown in Synthetic Examples, and may be purified by a normal crystallization, which is in striking contrast to the fact that the syntheses of phthalein phosphate, thymolphthalein phosphate, or thymolblue monophosphate require complicated operations for the isolation and the purification thereof, as described in the head of the present specification.

In the quantitative measurement of an alkaline phosphatase by using the compound of the present invention, the compound of the present invention may be substituted for disodium p-nitrophenyl phosphate in the Bessey-Lowry method, which is described in "Journal of Biological Chemistry", Vol. 164, p. 321 (1946), and the quantity of the azo dye A—N=N—B—OH released from the compound of the present invention may be measured instead of p-nitrophenol formed by the enzymatic reaction of the Bessey-Lowry method.

For example, the compound represented by the general formula (I) is dissolved in a buffer solution having a pH of around 10 to prepare a substrate solution. An activator of enzyme, such as magnesium chloride, may preferably be added to the substrate solution. Then, a solution containing an alkalne phosphatase to be measured was added to the substrate solution to carry out the reaction. At this time, the compound represented by the formula (I) may, preferably be contained in the substrate solution in the concentration of being from 1 to 20 mmol/l.

Preferably, the compound of the formula (I) may be present in large excess as compared with the alkaline phosphatase, that is, in a molar ratio of more than 10. The reaction described above may be conducted at a temperature ranging from 10° to 50° C., preferably from 30° to 40° C., for a period ranging from 10 to 60 minutes. Then, if necessary, the pH of the reaction solution may be raised or lowered by the addition of base or acid, and an organic solvent such as DMF, Methyl Cellosolve (trademark), or the like, may sometimes be added in order to stop the reaction. The density of the azo dye formed then may be measured by a spectrophotometer or the like, to determine the activity of the alkaline phosphatase, if needed, on the calibration curve.

The wavelength to be used in the colorimetry may be set in the region of the absorption maximum wavelenth of the dye. At the colorimetrical measurement, the addition of cyclodextrins, preferably α-cyclodextrin may shift the absorption maximum wavelength toward the longer wavelength. The amount of cyclodextrin added at this time, is in the range of from 0.1 to 20 mg, preferably from 1 to 10 mg per 1 ml of the solution to be colorimetrically measured.

Next, Synthetic Examples will be described with respect to typical compounds of the present invention represented by the general formula (I). Other compounds than those described hereinafter may also be synthesized with no difficulty according to the aforementioned synthetic process or the following descriptions.

SYNTHETIC EXAMPLE 1

Synthesis of Compound 13

Two ml of phosphorous oxychloride was mixed with 10 ml of acetone to prepare a solution which was then cooled to −9° C. To the solution, was added a solution of 1 g of 4-(4-nitrophenylazo)phenol in 4 ml of pyridine 4 ml of acetone and 3 ml of trimethyl phosphate over a period of 10 minutes. During the addition, the external cooling was conducted to maintain the temperature of the reaction liquid at below 0° C.

Then, 6 ml of water was dropped, and 2 g of ice was added to the solution, after which the resulting solution was agitated for 20 minutes at a room temperature. The reaction mixture was then poured into a mixture of 20 ml of saturated NaCl aqueous solution and a small amount of ice, and the crystals formed were collected by filtration. The crystals were dissolved in 1N—NaOH aqueous solution, the resulting solution was adjusted to pH 10, insolubles were removed by filtration, and the resulting filtrate was poured into 70 ml of ethanol, which was then agitated. The crystals thus formed were collected on a filter paper and washed with ethanol. Therresulting crystals were dissolved in 20 ml of water, which was added dropwise into 40 ml of ethanol. The yellow crystals thus formed were collected by filtration, washed with ethanol and then dried.

Yield 0.5 g, $\lambda_{max}^{0.02N-NaOH}$ 364 nm wherein $\lambda_{max}^{0.02N-NaOH}$ means the adsorption maximum wavelength of visible light or near ultraviolet in 0.02N—NaOH solution.

SYNTHETIC EXAMPLE 2

Synthesis of Compound 25

A solution of 5 g of 4-phenylazophenol (commercially available) in 20 ml of pyridine was dropped to a mixed solution of 10 ml of phosphorous oxychloride and 50 ml of acetone cooled to −7° C. During the addition, the exterior of the reaction vessel was cooled to maintain the temperature of the reaction liquid at below 0° C. After the addition was completed, agitation was conducted for 20 minutes at below 0° C., to which then 30 ml of water was added and agitation was continued for 10 minutes at a room temperature. The reaction mixture was then poured into 100 ml of a mixture of ice and a saturated NaCl aqueous solution and the crystals formed were collected by filtration. The crystals was dissolved in 35 ml of 1N—NaOH aqueous solution, which was then adjusted to pH 9. Insolubles were removed by filtration, the filtrate was poured into ethanol, the crystals formed were collected by filtration, washed with ethanol and then dried.

Yield 4.3 g (yellow crystals),
$\lambda_{max}^{0.02N-NaOH}$ 340 nm

SYNTHETIC EXAMPLE 3

Synthesis of Compound 3

Four ml of phosphorous oxychloride was mixed with 20 ml of acetone to prepare a solution which was then cooled to −8° C. To the solution, was dropped a solution of 2 g of 4-(2-methanesulfonyl-4-nitrophenylazo)-phenol in 20 ml of acetone, 10 ml of trimethyl phosphate, 8 ml of pyridine and 0.5 ml of triethylamine over a period of 25 minutes. During the addition, the external cooling was conducted to maintain the temperature of the reaction liquid at below 0° C. Further agitation was continued for 30 minutes at below 0° C., and 30 ml of water was then dropped thereto. The resulting solution was agitated for 10 minutes at a room temperature, and was then poured into 200 ml of a mixture of a saturated NaCl aqueous solution and ice, and the crystals formed were collected by filtration. The crystals were dissolved in 20 ml of 1N—NaOH aqueous solution, and the resulting solution was adjusted to pH of about 10. Insolubles were removed by filtration, and the resulting filtrate was poured into 150 ml of ethanol. The crystals thus formed were collected by filtration, washed with ethanol, and dried in vacuo.

Yield 2 g,
$\lambda_{max}^{0.02N-NaOH}$ 382 nm

The present invention will now be described according to the specific Examples with respect to the typical compounds. However, it is to be understood that the present invention shoud not be limited to the following Examples.

EXAMPLE 1

Preparation of a substrate solution:

Crystals of Compound 3 (35.05 mg) was dissolved in 10 ml of a glycine buffer (pH 10, 0.5 m mole/l of magnesium chloride contained therein).

Preparation of an enzyme solution:

The alkaline phosphatase Type I (produced by Sigma Chemical Co.), about 6 mg, was dissolved in 20 ml of distilled water to prepare an enzyme solution. The solution was diluted to ½ and ¼ respectively and thus, three kinds of enzyme solutions were prepared.

Procedure:

The substrate solution (1 ml) was charged in a test tube and heated at 37° C. for 3 minutes. The enzyme solution (0.1 ml) was added to the test tube and heated at 37° C. for 30 minutes to carry out the reaction and then, 10 ml of 0.02N—NaOH aqueous solution was added thereto to stop the reaction. A blank test solution was prepared by the same procedure as described above except that distilled water was substituted for the enzyme solution. Absorbance (ΔOD) was measured at 520 nm using the blank test solution as a control. The same procedure as described above was conducted with respect to each of three kinds of the enzyme solutions. Another absorbance (ΔOD) was measured at 410 nm with respect to each of the same enzyme solutions by the Bessey-Lowry method, in which the blank test solution also was used as a control.

The procedure of the Bessey-Lowry method is quite the same as described above except for a case where 20 mg of sodium p-nitrophenyl phosphate is substituted for 35.05 mg of the crystals of Compound 3 and the density of color is colorimetrically measured at 410 nm.

A relationship between the values of ΔOD obtained by these two methods is given in FIG. 1.

FIG. 1 discloses the followings:

(1) The ΔOD value measured by the present method varies in proportion to an enzyme concentration or the ΔOD value measured by the Bessey-Lowry method and thus, the former ΔOD value may be used to determine the activity of the enzyme.

(2) The ΔOD value measured by the method in which Compound 3 is used as a substrate is higher than the ΔOD value measured by the Bessey-Lowry method (the slope of the straight line is above 1) and thus, the sensitivity of the method in which Compound 3 is used as a substrate is higher than that of the Bessey-Lowry method.

(3) In the case where Compound 3 is used as a substrate, a colorimetry may be conducted at 520 nm and thus, this method has less susceptibility to interference with a colored substance such as a pigment in blood than the Bessey-Lowry method in which a colorimetry is conducted at 410 nm.

Thus, it can be seen that the compound of the present invention is a suitable one for a substrate to be used in a method for the quantitative analysis of an alkaline phosphatase.

EXAMPLE 2

The procedure of Example 1 was repeated except that 22.5 mg of the crystals of Compound 25 was substituted for 35.05 mg of the crystals of Compound 3 of Example 1, and the measurement of the absorbance (ΔOD) was conducted at 430 nm instead of 520 nm. The results are given in FIG. 2.

Figure 2:
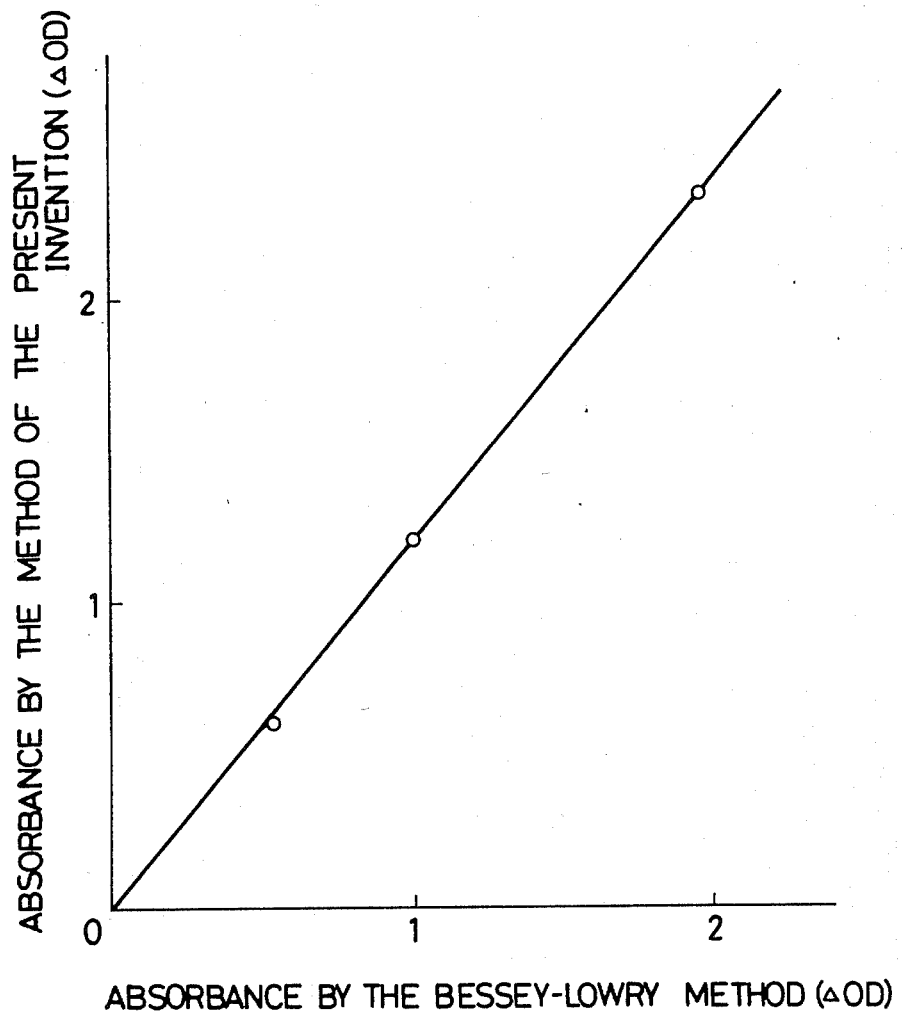

FIG. 2 discloses the followings:

(1) The ΔOD value measured by the present method varies in proportion to an enzyme concentration or the ΔOD value measured by the Bessey-Lowry method and thus, the former ΔOD value may be used to determine the activity of the enzyme.

(2) The ΔOD value measured by the method in which Compound 25 is used as a substrate is higher than the ΔOD value measured by the Bessey-Lowry method (the slope of the straight line is above 1) and thus, the sensitivity of the method in which Compound 25 is used as a substrate is higher than that of the Bessey-Lowry method.

Thus, it can be seen that the compound of the present invention is a suitable one for a substrate to be used in a method for the quantitative analysis of an alkaline phosphatase.

EXAMPLE 3

The procedure of Example 1 was repeated except that 30 mg of the crystals of Compound 13 was substituted for 35.05 mg of the crystals of Compound 3 of Example 1, and the measurement of the absorbance was conducted at 500 nm instead of 520 nm. The results are given in FIG. 3.

Figure 3:
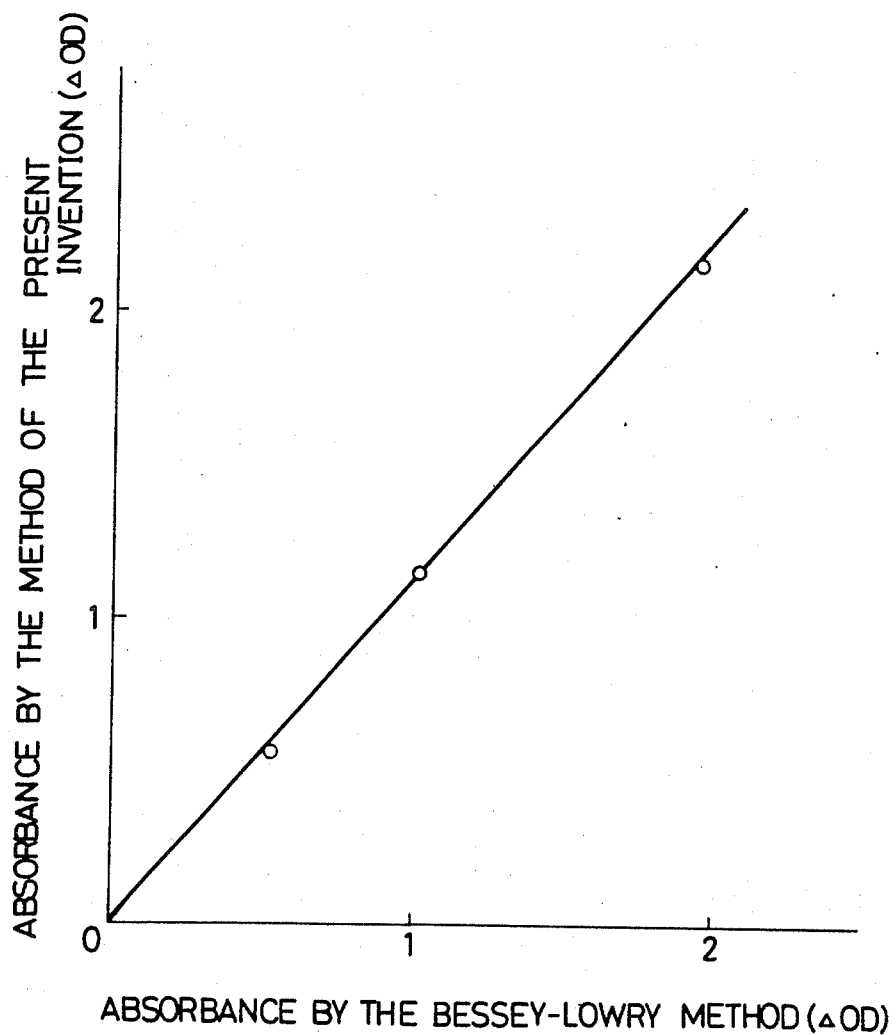

FIG. 3 discloses the followings:

(1) the ΔOD value measured by the present method varies in proportion to an enzyme concentration or the ΔOD value measured by the Bessey-Lowry method and thus, the former ΔOD value may be used to determine the activity of the enzyme.

(2) The ΔOD value measured by the method in which Compound 13 is used as a substrate is higher than the ΔOD value measured by the Bessey-Lowry method (the slope of the straight line is above 1) and thus, the sensitivity of the method in which Compound 13 is used as a substrate is higher than that of the Bessey-Lowry method.

(3) In the case where Compound 13 is used as a substrate, a colorimetry may be conducted at 500 nm and thus, this method has less susceptibility to interference with a colored substance such as a pigment in blood than the Bessey-Lowry method in which a colorimetry is conducted at 410 nm.

Thus, it can be seen that the compound of the present invention is a suitable one for a substrate to be used in a method for the quantitative analysis of an alkaline phosphatase.

EXAMPLE 4

The procedure of Example 1 was repeated except that 48.18 mg of the crystals of Compound 35 was substituted for 35.05 mg of the crystals of Compound 3 of Example 1, and the measurement of the absorbance was conducted at 644 nm instead of 520 nm. The results are given in FIG. 4.

Figure 4:
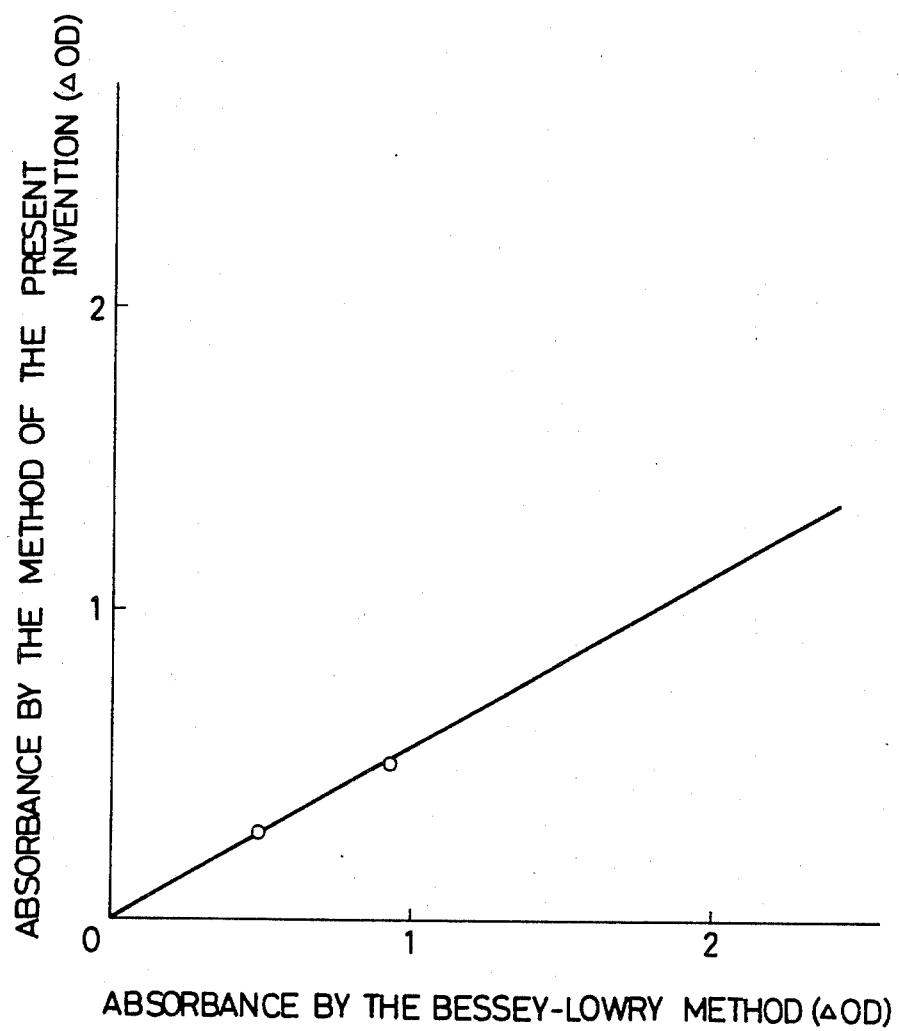

FIG. 4 descloses the followings:

(1) The ΔOD value measured by the present method varies in proportion to an enzyme concentration or the ΔOD value measured by the Bessey-Lowry method and thus, the former ΔOD value may be used to determine the activity of the enzyme.

(2) In the case where Compound 35 is used as a substrate, a colorimetry may be conducted at 644 nm and thus, this method has less susceptibility to interference with a colored substance such as a pigment in blood than the Bessey-Lowry method in which a colorimetry is conducted at 410 nm.

Thus, it can be seen that the compound of the present invention is a suitable one for a substrate to be used in a method for the quantitative analysis of an alkaline phosphatase.

EXAMPLE 5

The procedure of Example 1 was repeated except that 33.4 mg of the crystals of Compound 5 was substituted for 35.05 mg of the crystals of Compound 3 of Example 1, and the measurement of the absorbance (ΔOD) was conducted at 512 nm instead of 520 nm. The results are given in FIG. 5.

Figure 5:
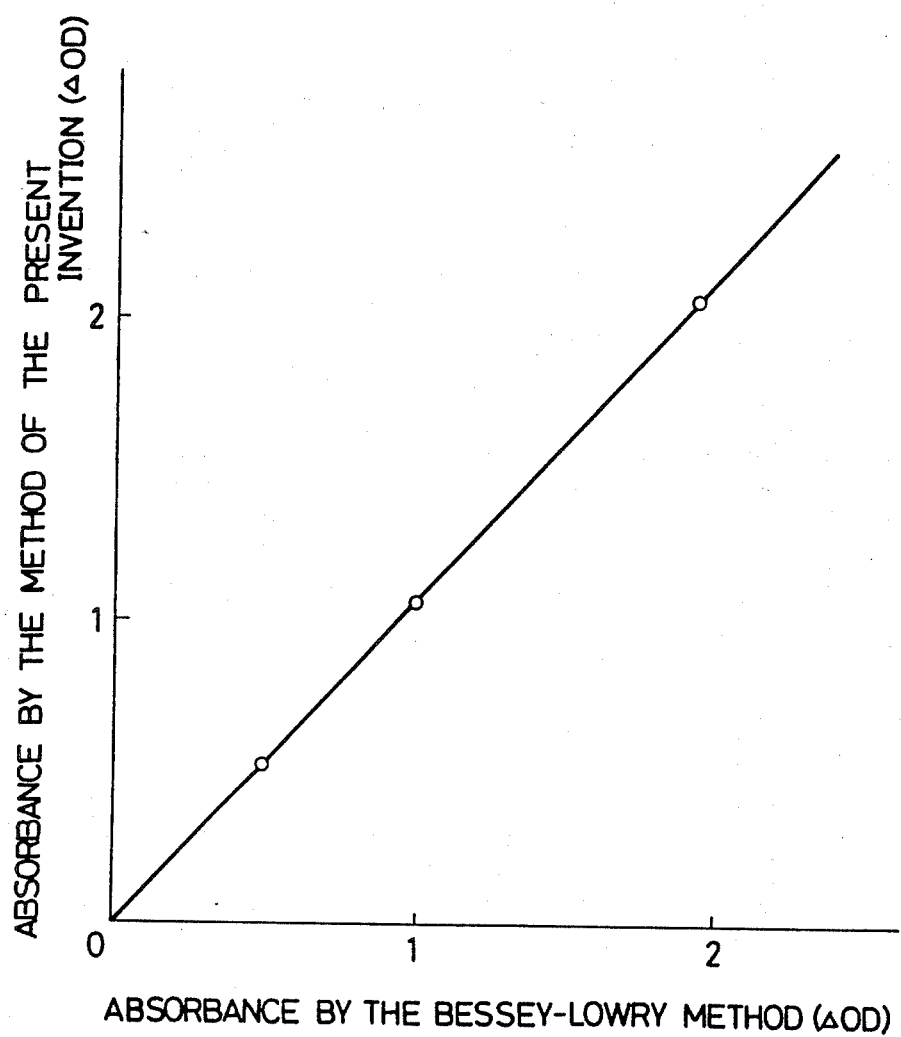

FIG. 5 discloses the followings:

(1) The ΔOD value measured by the present method varies in proportion to an enzyme concentration or the ΔOD value measured by the Bessey-Lowry method and thus, the former ΔOD value may be used to determine the activity of the enzyme.

(2) The ΔOD value measured by the method in which Compound 5 is used as a substrate is higher than the ΔOD value measured by the Bessey-Lowry method (the slope of the straight line is above 1) and thus, the sensitivity of the method in which Compound 5 is used as a substrate is higher than that of the Bessey-Lowry method.

(3) In the case where Compound 5 is used as a substrate, a colorimetry may be conducted at 512 nm and thus, this method has less susceptibility to interferene with a colored substance such as a pigment in blood than the Bessey-Lowry method in which a colorimetry is conducted at 410 nm.

What is claimed is:

1. A phosphoric ester selected from the group consisting of:

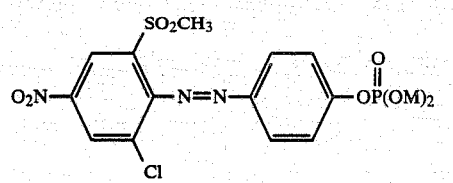

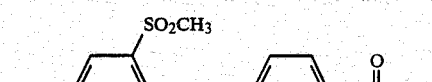

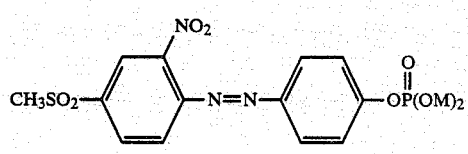

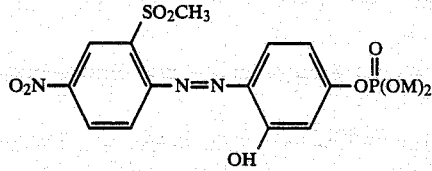

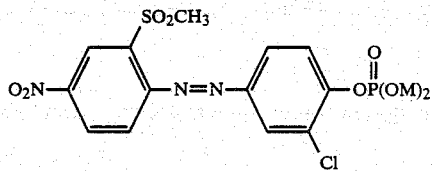

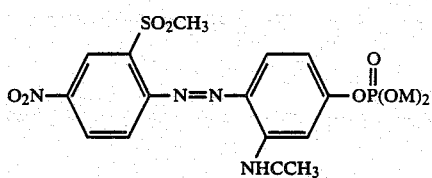

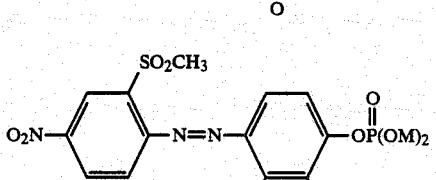

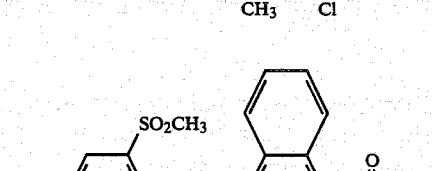

-continued

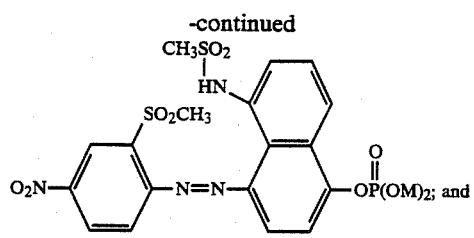

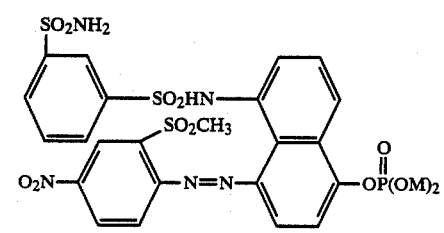

wherein M is hydrogen, sodium or potassium.

2. The phosphoric ester which is

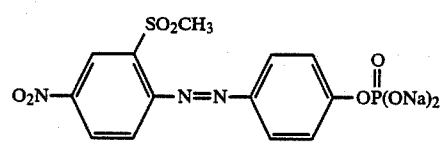

3. The phosphoric ester which is

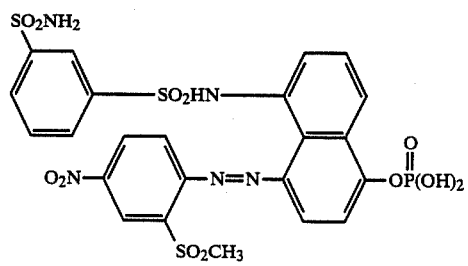

4. The phosphoric ester of claim 1, which is of the formula:

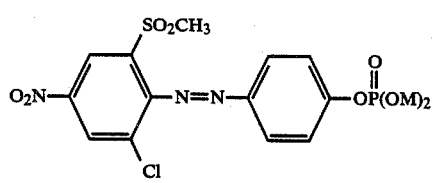

wherein M is hydrogen, sodium or potassium.

5. The phosphoric ester of claim 1, which is of the formula:

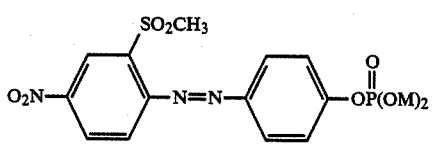

wherein M is hydrogen, sodium or potassium.

6. The phosphoric ester of claim 1, which is of the formula:

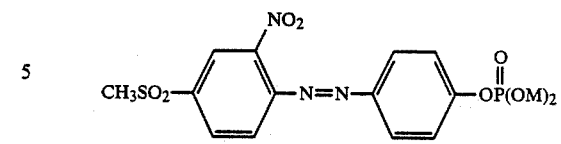

wherein M is hydrogen, sodium or potassium.

7. The phosphoric ester of claim 1, which is of the formula:

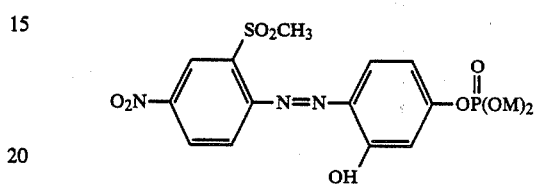

wherein M is hydrogen, sodium or potassium.

8. The phosphoric ester of claim 1, which is of the formula:

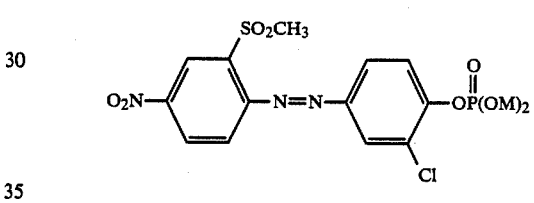

wherein M is hydrogen, sodium or potassium.

9. The phosphoric ester of claim 1, which is of the formula:

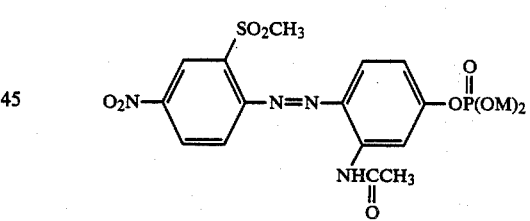

wherein M is hydrogen, sodium or potassium.

10. The phosphoric ester of claim 1, which is of the formula:

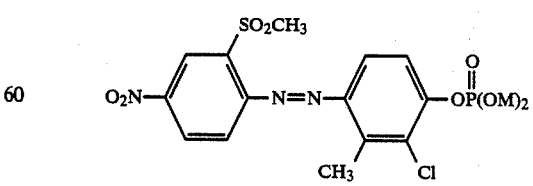

wherein M is hydrogen, sodium or potassium.

11. The phosphoric ester of claim 1, which is of the formula:

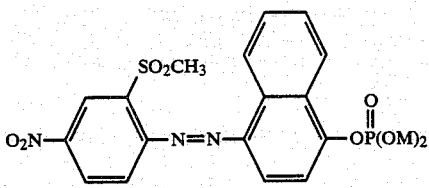
wherein M is hydrogen, sodium or potassium.
12. The phosphoric ester of claim 1, which is of the formula:
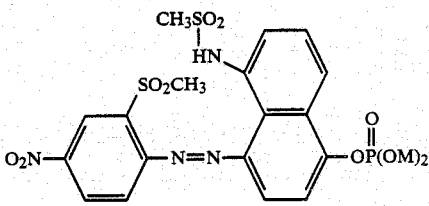
wherein M is hydrogen, sodium or potassium.
13. The phosphoric ester of claim 1, which is of the formula:
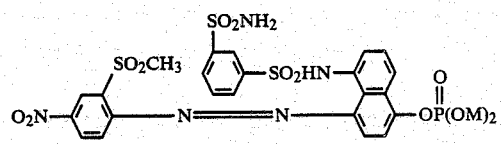
wherein M is hydrogen, sodium or potassium.
* * * * *